United States Patent [19]

Nakamura

[11] Patent Number: 4,631,227
[45] Date of Patent: Dec. 23, 1986

[54] TOILET ARTICLE

[76] Inventor: Kenji Nakamura, 3-7, Higashiyodogawa-ku, Osaka, Japan

[21] Appl. No.: 558,114

[22] Filed: Dec. 5, 1983

[30] Foreign Application Priority Data

Dec. 8, 1982 [JP] Japan ................. 57-213930

[51] Int. Cl.$^4$ .............. A47L 13/16; A47L 17/00; B32B 3/00; B32B 5/22
[52] U.S. Cl. .................... 428/283; 128/156; 15/118; 428/913; 428/286; 428/246; 424/28
[58] Field of Search ............. 128/640–641, 128/155, 156; 428/198, 913, 286, 246; 424/28; 15/118

[56] References Cited

U.S. PATENT DOCUMENTS

| | | | |
|---|---|---|---|
| B 494,439 | 4/1976 | Gross | 128/156 |
| B 494,450 | 2/1976 | Gross | 128/156 |
| 2,137,169 | 11/1938 | Levey | 128/156 |
| 3,249,109 | 5/1966 | Maeth et al. | 128/156 |
| 3,339,546 | 9/1967 | Chen | 128/156 |
| 3,475,363 | 10/1969 | Sander | 128/156 X |
| 3,598,123 | 8/1971 | Zaffaroni | 604/897 |
| 3,731,683 | 5/1973 | Zaffaroni | 604/304 X |
| 3,742,951 | 7/1973 | Zaffaroni | 604/304 X |
| 3,755,558 | 8/1973 | Scribner | 604/289 X |
| 3,787,494 | 1/1974 | Alouin et al. | 564/189 |
| 3,867,520 | 2/1975 | Mori et al. | 604/304 X |
| 3,995,632 | 12/1976 | Nakano et al. | 604/892 |
| 4,031,894 | 6/1977 | Urquhart et al. | 604/897 |
| 4,060,084 | 11/1977 | Chandrasekaran et al. | 428/28 X |
| 4,125,110 | 11/1978 | Hymes | 128/641 |
| 4,136,145 | 1/1979 | Fuchs et al. | 424/22 X |
| 4,253,460 | 3/1981 | Chen et al. | 128/283 |
| 4,274,420 | 6/1981 | Hymes | 128/641 |
| 4,295,987 | 10/1981 | Parks | 252/194 |
| 4,409,206 | 10/1983 | Stricker | 424/28 X |
| 4,473,611 | 9/1984 | Haq | 428/246 X |

Primary Examiner—Nancy Swisher
Attorney, Agent, or Firm—Burgess, Ryan & Wayne

[57] ABSTRACT

A toilet article comprises a sheet-like material (1), a pressure sensitive adhesive layer (2) formed on the sheet-like material (1) and hydrogel formable polymer layer (3) formed on the surface of the pressure sensitive adhesive layer (2).

The sheet-like material (1) may be a film obtained from flexible synthetic resin such as polyethylene, polypropylene, polyester, polyamide, polyurethane, polyvinyl alcohol, rayon, polyvinyl chloride, a sheet of an unwoven fabric or a woven fabric, or a porous film.

The pressure sensitive adhesive layer (2) is sticky and may be an acrylic resin adhesive, a polyester resin adhesive, a rubber adhesive or an elastomeric adhesive.

The hydrogel formable polymer is a substance which forms gel when water is applied to it and has a water retention characteristic of between ten times and one hundred times.

Typically, usable hydrogel substances are crosslinked substances of alkali metal salt of carboxymethylcellulose, alkali metal salt of polyacrylic acid, crosslinked substance of polyalkylene oxide, cellulose, carboxylic alkali metal salt formed from acrylonitrile graft polymer, starch-acrylonitrile substance, any of which has a good water absorbent and water retention.

The hydrogel formable polymer layer may have cosmetics in a water free condition contained therein or coated on the surface thereof.

11 Claims, 11 Drawing Figures

TOILET ARTICLE

TECHNICAL FIELD TO WHICH THE INVENTION RELATES

The present invention relates to a toilet article which is used to care for the skin.

BACKGROUND OF THE INVENTION

Recently, many kinds of cosmetics having chemical agents, with effects for refreshing the skin mixed therein, have been used. The purpose for using such cosmetics are to refresh the skin because of the absorption of the chemical agents contained in the cosmetics through the skin and to enhance the effects of make-up by refreshing the skin. These cosmetics are made in forms of lotion, milky lotion or cream and are mainly applied to a portion of the face, which portion may easily be wrinkled.

According to the characteristic usage of these cosmetics containing the chemical agents, the cosmetics are applied to the bare skin, after make-up is removed, and they are left on the skin for a relatively long time so as to achieve the refreshing effects of the skin. Accordingly, the cosmetics are used to care for the skin before going sleep so as to refresh the skin during a sleep, or they are used as facial packs when the face is packed. These cosmetics are usually sold under the name of a night lotion or a night cream, or pack.

Taking into consideration the objects of using such cosmetics, the refreshment of the skin can be effectively achieved if the applied cosmetics are not easily dried by virtue of a body temperature and if the skin is readily brought into a condition suitable for absorbing the cosmetics.

However, commonly spread usage of such cosmetics has problems that the applied cosmetics are easily dried by virtue of a body temperature, which results in decrease of the effects of cosmetics, and that the cosmetics are rubbed off onto clothing or bed linen during a sleep and that the effects of the cosmetics are lost.

OBJECTS OF THE INVENTION

The present invention has been developed taking into consideration the circumstances described above.

An object of the present invention is to provide a toilet article which serves to prevent the applied cosmetics from being easily dried by virtue of a body temperature, which maintains effects of the cosmetics for a long time, and which effectively achieves the pack effects. Some examples of the pack effects referred to above are prevention of moisture evaporation from the surface of the skin, plasticization of the outer dead layer of the epidermis and expansion of pores in the skin so as to facilitate the absorption of the valid ingredients into the skin, and removement skin debris and blackheads from the face, when the pack is removed.

Another object of the present invention is to provide a toilet article by which cosmetics applied to the skin are free from rubbing off onto clothing or bed linen in use and by which effects brought about by the cosmetics to the skin can be lasted for a long time.

At first, in order to achieve the above-described objects of the present invention, the present inventor prepared a toilet article. The toilet article comprised a sheet having a pressure sensitive adhesive agent coated thereon, and a fibrous sheet, such as a sheet of gauze, a sheet of flannel, an unwoven fabric sheet or a cotton sheet, adhered to a part of the pressure sensitive adhesive agent. After cosmetics were applied to the adhered fibrous sheet of the toilet article, the article was adhered to the objective portion of a person. Then, the effects of the toilet article were investigated.

As a result, the inventor found that the pressure sensitive adhesive sheet had achieved advantages in that the article was surely adhered to an objective portion. However, he also found that, although the fibrous sheet was used to retain cosmetics therein, its capability for retaining cosmetics was insufficient. Accordingly, the article could not be practically used, if the cosmetics were of lotion type or of milky lotion type, because the cosmetics oozed out or dripped.

The present inventor has further conducted various investigations and has found the following matters.

(1) A polymer which forms gel when water is applied thereto can be effectively utilized as a material for retaining cosmetics therein.

(2) Such a polymer can retain the cosmetics free from oozing.

(3) The basic pressure sensitive adhesive sheet is adopted to prevent a toilet article from slipping down.

The term "hydrogel formable polymer" will be used in this specification to refer to a polymer which forms gel when water is applied thereto.

SUMMARY OF THE INVENTION

According to the present invention, the above-described objects are achieved by a toilet article comprising a sheet-like material, an adhesive layer formed on the sheet-like material, and a layer of hydrogel formable polymer formed on the adhesive layer.

It is preferable that the toilet article according to the present invention includes a releasing sheet adhered thereto and covering the hydrogel formable polymer layer and the adhesive layer before the toilet article is used.

BRIEF DESCRIPTION OF THE DRAWINGS

The present invention will now be explained in detail with reference to some embodiments thereof illustrated in the accompanying drawings, wherein.

DETAILED DESCRIPTION OF THE EMBODIMENTS

Figure 1:
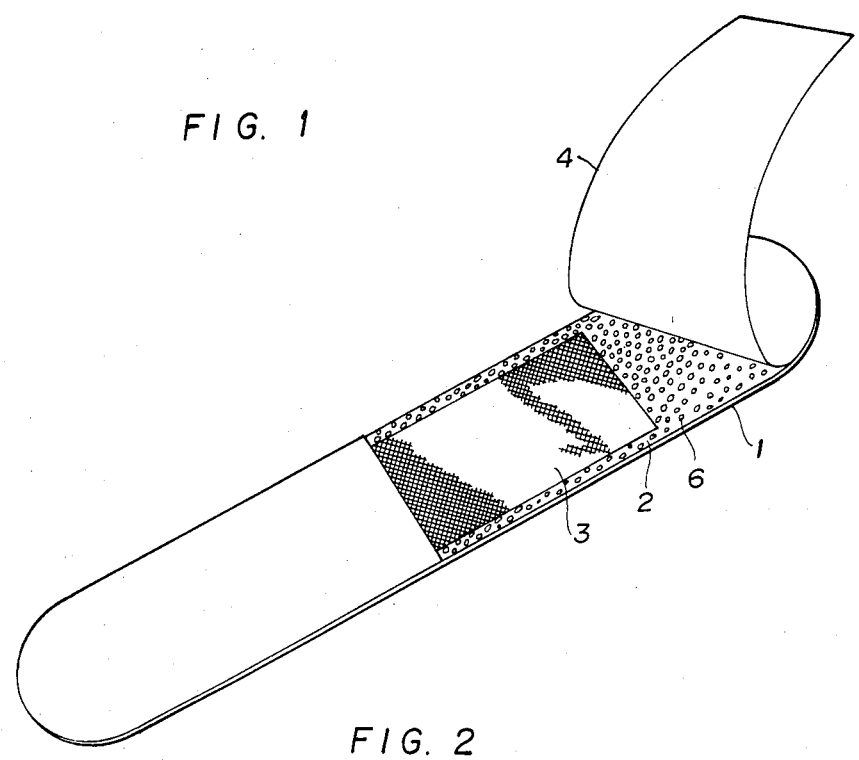
FIG. 1 is a perspective view of an embodiment of a toilet article of the present invention.
Figure 2:
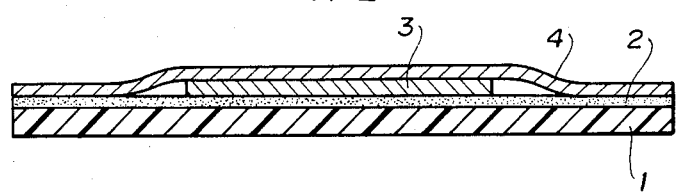
FIG. 2 is a cross sectional view of an embodiment of a toilet article of the present invention.

Referring to FIGS. 1 and 2, the basic construction of the toilet article of the present invention comprises a sheet-like material 1 and a pressure sensitive adhesive layer 2 formed on the sheet-like material 1.

The sheet-like material 1 may be a film obtained from flexible synthetic resin such as polyethylene, polypropylene, polyester, polyamide, polyurethane, polyvinyl alcohol, rayon, polyvinyl chloride, a sheet of an unwoven fabric or a woven fabric, or a porous film. The pressure sensitive adhesive layer 2 is sticky and may be a acrylic resin adhesive, a polyester resin adhesive, a rubber adhesive or an elastomeric adhesive.

The sheet-like material 1 may be a non-porous film, however, it is preferable that the sheet-like material is a film having ventilating pores 6 formed thereon by means of hot needles, or that it is made of an unwoven fabric or a woven fabric so as to form ventilating pores 6 therein, since cutaneous respiration is not prevented when such an article is applied to the skin.

The the pressure sensitive adhesive layer 2 is formed on the sheet-like material 1 by means of a roll coat method, a knife coat method or a printing method. A part of the pressure sensitive adhesive layer 2 serves to adhere the article to the skin.

A hydrogel formable polymer layer 3 is formed on the surface of the pressure sensitive adhesive layer 2 in the embodiment illustrated in FIG. 2.

The hydrogel formable polymer, which is utilized in the present invention, is a substance which forms gel when water is applied to it and has a water retention characteristic of between ten times and almost one hundred times. The water retention characteristic is a ratio of the weight of water retained in the substance to that of the substance per se, after the substance is dipped into water to absorb water therein and is thereafter centrifugally dehydrated. Accordingly, even when the hydrogel formable polymer is subjected to a some external pressure, liquid which has been absorbed therein will not be easily discharged. Taking the fact into consideration that the water retention characteristic of cotton or pulp is about four times, it can be concluded that the hydrogel has superior water absorption and retention characteristics when it is compared with usual fibers which absorb or retain water between or within fibers.

Hydrogel substances which are usable in the present invention may be those disclosed in Japanese Patent Application Laid-open No. 15458/81 or in Japanese Patent Publication No. 17965/72. Typically, usable hydrogel substances are crosslinked substances of alkali metal salt of carboxymethylcellulose, alkali metal salt of polyacrylic acid, crosslinked substance of polyalkylene oxide, carboxylic alkali metal salt formed from cellulose-acrylonitrile graft polymer, carboxylic alkali metal salt formed from starch-acrylonitrile graft polymer and the like, any of which has a good water absorption and water retention.

As described above, the hydrogel formable polymer utilized in the present invention forms gel when water is applied to it and has good water absorption and retention characteristics. Hydrogel substance usually takes the form of either a sheet or powder under the conditions wherein it is dry.

The hydrogel formable polymer formed in a sheet is more preferable for the embodiment illustrated in FIG. 2. After the sheet-like hydrogel formable polymer is cut in a predetermined size, it is adhered on the surface of the pressure sensitive adhesive layer 2. In this instance, if the hydrogel formable polymer layer 3 is adhered to the entire surface of the pressure sensitive adhesive layer 2, there remains no means for securing the toilet article to the skin. Therefore, it is preferable that the hydrogel formable polymer layer 3 is formed in such manner that a part of the pressure sensitive adhesive layer 2 is not covered by the hydrogel formable polymer. Contrary to this, when the hydrogel formable polymer layer 3 is adhered to the entire surface of the pressure sensitive adhesive layer 2, it is recommended to use another means appropriate for securing the toilet article to the skin, such as a strand-like material or a tape-like material having adhesive coated thereon and having an appropriate shape for the purpose.

Then, a releasing sheet 4 is provided so as to cover both the hydrogel formable polymer layer 3 and the pressure sensitive adhesive layer 2.

It is preferable that the releasing sheet 4 is a sheet or a film. When the releasing sheet 4 is a sheet, it is made of paper or cellophane having non-adhesive material, such as wax, parafin was, or silicone oil, absorbed therein or coated thereon. When the releasing sheet is a film, it is made of a simple substance of film, such as polyester, polypropylene or polyethylene, or a sheet obtained from such a film by coating on the surface thereof with silicone resin or fluoroplastic.

With respect to the covering construction, it is desirable that the releasing sheet 4 covers both the hydrogel formable polymer layer 3 and the pressure sensitive adhesive layer 2.

The number of the releasing sheets 4 may be one. In some cases, as illustrated in FIG. 1, two sheets 4 may be used to cover from both the ends to the center and overlap with each other at the center of the toilet article so as to facilitate easy releasing of the sheets 4 from the layers 2 and 3 upon use of the toilet article.

Figure 3:
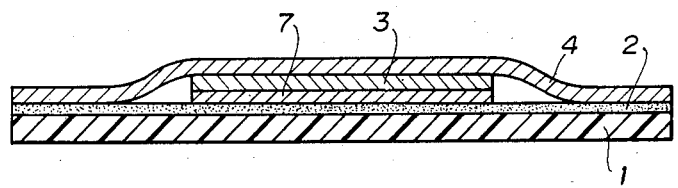
FIG. 3 is a cross sectional view of an embodiment of a toilet article of the present invention wherein a porous layer is formed between a pressure sensitive adhesive layer and a hydrogel formable polymer layer.

FIG. 3 illustrates another embodiment of the present invention. In this embodiment, a pressure sensitive adhesive layer 2 is formed on the surface of a sheet-like material 1, and a porous layer 7 is formed on the pressure sensitive adhesive layer 2. A layer 3 of a hydrogel formable polymer is formed on the porous layer 7. Both the hydrogel formable polymer layer 3 and the pressure sensitive adhesive layer 2 are covered by a releasing sheet 4.

When the porous layer 7 is formed between the pressure sensitive adhesive layer 2 and the hydrogel formable polymer layer 3 as illustrated in FIG. 3, the fixation of the hydrogel formable polymer 3 is further ensured, and the water absorption and retention characteristics of the hydrogel formable polymer layer 3 can further be enhanced. It is because the hydrogel formable polymer layer 3 does not contact the pressure sensitive adhesive in this embodiment and, accordingly, the characteristics are increased.

It is preferable that the porous layer 7 is a sheet of gauze, a cotton sheet, a woven fabric, an unwoven fabric, paper, or thin foamed sponge. In order to fix the porous layer 7 to the hydrogel formable polymer layer 3, they are superimposed with each other and are punched. As a result of the punching operation, the peripheral edges of the porous layer 7 and the hydrogel formable polymer layer 3 are strongly pressed against each other and are bonded to each other. If necessary, adhesive may be applied between the porous layer 7 and the hydrogel formable polymer layer 3 to ensure their bonding.

Figure 4:
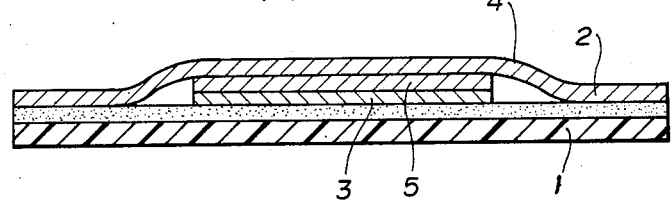
FIG. 4 a cross sectional view of an embodiment of a toilet article of the present invention wherein a porous layer is formed between a hydrogel formable polymer layer and a releasing sheet.

In the embodiment illustrated in FIG. 4, a pressure sensitive adhesive layer 2 is formed on the surface of the sheet-like material 1, and a layer 3 of a hydrogel formable polymer is adhered to the pressure sensitive adhesive layer 2. A porous layer 5 is formed on the hydrogel formable polymer layer 3. A releasing sheet 4 covers both the porous layer 5 and the pressure sensitive adhesive layer 2.

If the porous layer 5 is formed on the hydrogel formable polymer layer 3 as described above, good feelings can be created in use of the toilet article because, when the toilet article of the present invention is used, the porous layer, instead of the hydrogel formable polymer layer 3, contacts the skin and gives a light and soft touch to the user.

The porous layer 5 illustrated in FIG. 4 has a construction similar to that of the porous layer 7 illustrated in FIG. 3. The porous layer 5 can be fixed to the hydrogel formable polymer layer 3 by way of the fixing method similar to that explained with reference to FIG. 3.

Figure 5:
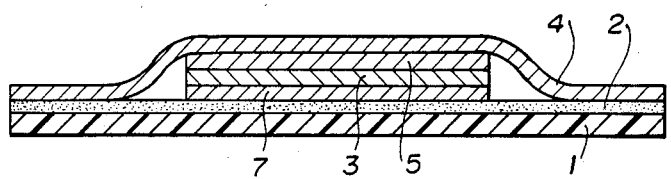
FIG. 5 is a cross sectional view of an embodiment of a toilet article of the present invention wherein a porous layer is formed between a pressure sensitive adhesive layer and a hydrogel formable polymer layer and another porous layer is formed between the hydrogel formable polymer layer and a releasing sheet.

The embodiment illustrated in FIG. 5 has both the characteristics of those illustrated in FIGS. 3 and 4. In this embodiment, the hydrogel formable polymer layer 3 is formed between two porous layers 5 and 7. More specifically, the hydrogel formable polymer 3 is positioned on the porous material 7, and then, the porous material 5 is positioned on the hydrogel formable polymer 3. After they are superimposed, they are cut by means of a press into a predetermined size. The thus obtained article is adhered to a pressure sensitive adhesive layer 2.

In this instance, the adjacent layers are bonded to each other as a result of the pressing. If adhesive is dotted between the layers, the layers are surely adhered to each other.

Figure 6:
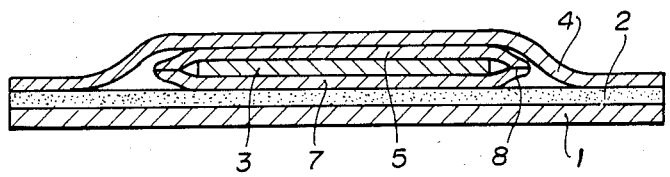
FIG. 6 is a cross sectional view of an embodiment of a toilet article of the present invention wherein a bonded portion is formed at a peripheral portion where the porous layers are superimposed.

The embodiment illustrated in FIG. 6 has a construction similar to that illustrated in FIG. 5 wherein a layer 3 of a hydrogel formable polymer is formed between two porous materials 5 and 7. This embodiment can achieve the advantages similar to those achieved by the embodiment illustrated in FIG. 5, however, it is manufactured by a method different from that for manufacturing the embodiment illustrated in FIG. 5. More specifically, the two porous materials are formed into a bag, and the hydrogel formable polymer is contained in the bag. Thereafter, a pressure sensitive adhesive layer is attached to the bag. According to this method, the productivity for forming bag is enhanced if materials used as the porous materials 5 and 7 contain thermoplastic resin with hot melt adhesion, or if the surfaces of the porous materials 5 and 7 are coated with the resin described just above.

Some cosmetic drugs may be contained in the bag together with the hydrogel formable polymer, if necessary. As a result of the containing of such cosmetic drugs, the effects of the toilet article will be increased.

The toilet article of the present invention is manufactured in a manner described above, and when it is used, the releasing sheet 4 is first removed from the article, and then the objective cosmetics, which will be explained later, is applied to or absorbed into the hydrogel formable polymer layer 3 or the surface of the first porous layer 5. When one or more porous layers are prepared, the cosmetics are contacted with the hydrogel formable polymer layer 3 by slightly pressing the porous layers by means of a finger.

The cosmetics used here contain water, and it is preferable that the cosmetics are prepared with drugs for refreshing the skin, for example, vitamins, amino acids, enzymes, or substance having attribute to adsorb grease and dirt from the facial skin, for example, talc, kaolin, or adsorptive clays.

As a result of the application or absorption of the cosmetics, the hydrogel formable polymer layer forms gel and swells due to the water contained in such cosmetics as described above.

Under this condition, the toilet article is applied to the objective portion of the face, and the peripheral portion of the pressure sensitive adhesive layer is urged to the skin by pressing the article on the back of the sheet-like material so as to fix the article there. The toilet article of the present invention thus having been fixed on the skin is not easily removed from the skin and is stably adhered to the skin during sleeping.

Figure 7:
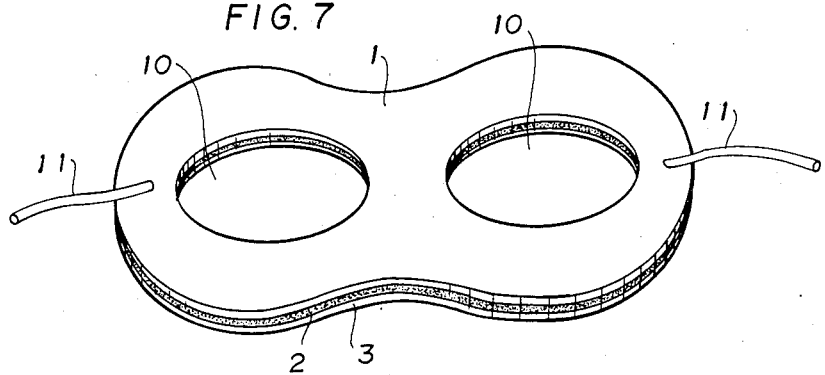
FIGS. 7 and 8 are perspective views of other embodiments of the present invention.
Figure 8:
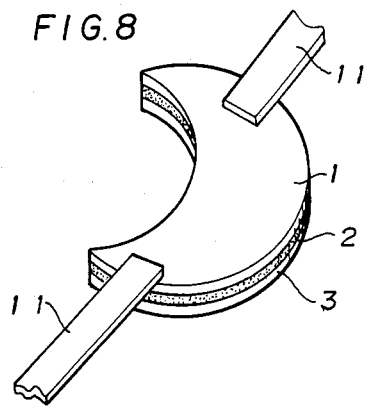

FIGS. 7 and 8 illustrate other embodiments. In these embodiments, the hydrogel formable polymer layer 3 is adhered to the entire surface of the sheet-like material 1 by means of the adhesive layer 2 which is formed on the sheet-like material 1. The adhesive of the layer 2 is not limited to a pressure sensitive adhesive but may be any suitable ones.

The embodiment illustrated in FIG. 7 is formed in a mask shape which has openings 10 formed at positions corresponding to eyes of a person.

FIG. 8 illustrates an embodiment which is suitable for being applied to the corner of the eye of a person.

In the embodiments illustrated in FIGS. 7 and 8, a suitable means for fixing the article to the skin is further prepared, because the hydrogel formable polymer layer 3 covers the entire surface of the sheet-like material 1.

The fixing means 11 may be an elongated material, such as a strand-like material having pressure sensitive adhesive coated thereon as illustrated in FIG. 7, a tape-like material having pressure sensitive adhesive coated thereon as illustrated in FIG. 8, or sheet-like material formed in a suitable form and having pressure sensitive adhesive coated thereon. It is also possible to prepare a plurality of, for example, two strand-like material or tape-like materials, one ends of which are capable of being fixed to the sheet-like material 1, and fasten the free ends of the strand-like materials or tape-like materials to each other so as to fix the article on the face. The methods described above are especially useful for the embodiment formed in a mask shape as illustrated in FIG. 7. Further, when the article is formed in a mask shape, it is also possible to put a flexible ring band on a head of a person to fix the mask which has covered the face of the person.

As will be apparent from the above-description, the fixing means 11 may have previously been secured to the sheet-like material 1. The fixing means 11 may be attached to the sheet-like material when the article is used.

When the toilet articles illustrated in FIGS. 7 and 8 are manufactured, an adhesive layer 2 is formed by coating or printing on one side of the sheet-like material 1. It must be noted that, in some cases, the sheet-like material 1 may be continuous. Then, a sheet-like hydrogel formable polymer layer 3 is adhered to the thus formed adhesive layer 2. The superimposed materials are cut in a desired shape by means of a press. Fixing means may be secured to the toilet article or may not be secured to the latter.

Figure 9:
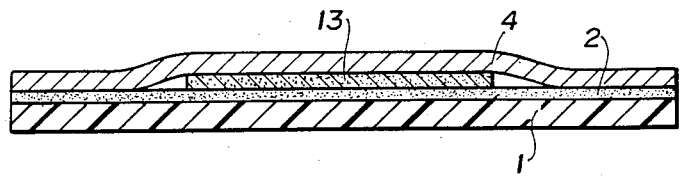
FIG. 9 is a perspective view of an embodiment of a toilet article of the present invention.

FIG. 9 illustrates another embodiment of the present invention. In this embodiment, a sticky pressure sensitive adhesive layer 2 is formed on a sheet-like material 1. A hydrogel formable polymer layer 13, which contains cosmetics in a water free condition, is formed on the surface of the pressure sensitive adhesive layer 2. The hydrogel formable polymer layer 13 and the pressure sensitive adhesive layer 2 are covered by a releasing sheet 4.

The cosmetics used in this embodiment is powder, granule, or paste and is in a condition free from water, which condition will be referred to as "water free condition" in this specification. However, oil may be contained in the cosmetics.

It is preferable that the cosmetics used here are prepared with drugs for refreshing the skin, for example, vitamins, amino acids, enzymes, or substance having attribute to adsorb grease and dirt from the facial skin, for example, talc, kaolin, or adsorptive clays.

In the embodiment illustrated in FIG. 9, it is preferable to use powder of hydrogel formable polymer so as to facilitate mixing of the cosmetics therewith.

Figure 10:
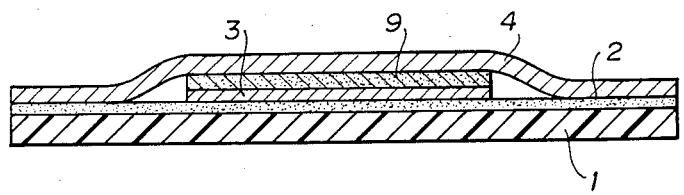
FIG. 10 is a cross sectional view of an embodiment of a toilet article of the present invention.

FIG. 10 is a cross sectional view illustrating still another embodiment of the present invention. In this embodiment, a pressure sensitive adhesive layer 2 is formed on a sheet-like material 1 and has a hydrogel formable polymer layer 3 attached on the surface thereof. A layer 9 of cosmetics in a water free condition is formed on the surface of the hydrogel formable polymer layer 3. It is preferable in this embodiment that the hydrogel formable polymer is formed in a sheet and that the cosmetics 9 is coated on the surface of the sheet of the hydrogel formable polymer 3. The sheet-like hydrogel formable polymer 3 with the layer 9 of the cosmetics is cut in a predetermined size, and then, the cut hydrogel formable polymer 3 is adhered to the pressure sensitive adhesive layer 2 while a part of the pressure sensitive adhesive layer 2 is left uncovered. The sheet-like hydrogel formable polymer 3 with the layer 9 of the cosmetics and the pressure sensitive adhesive layer 2 are covered by a releasing sheet 4.

Figure 11:
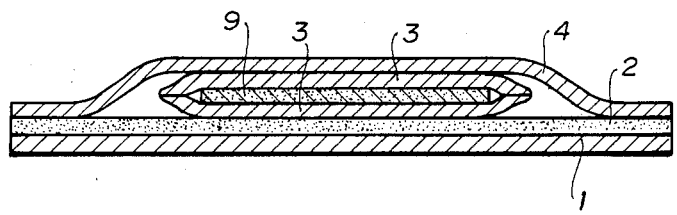
FIG. 11 is a cross sectional view of an embodiment of a toilet article of the present invention wherein a layer of cosmetics is formed between two hydrogel formable polymer layers.

In an embodiment illustrated in FIG. 11, a layer 9 of cosmetics is formed between two hydrogel formable polymer layers 3.

This embodiment is obtained: after formation of the cosmetic layer 9 on the first hydrogel formable polymer 3, positioning the second hydrogel formable polymer 3 on the cosmetic layer 9: and then, cutting the superimposed layers by means of a press into a predetermined size; and adhering the thus obtained article to a pressure sensitive adhesive layer.

In this instance, the adjacent layers are bonded to each other as a result of the pressing. If small amount of adhesive is dotted between the adjacent layers, the layers are surely adhered to each other.

In an alternative method, in place of overlapping the first and second hydrogel formable polymer 3, the first and second hydrogel formable polymers are formed in a bag while cosmetics 9, which are for example in a powder condition, are contained in the bag, and thereafter, a pressure sensitive adhesive layer is attached to the bag.

A releasing sheet 4 covers the hydrogel formable polymer layers 3 and the pressure sensitive adhesive layer 2.

When the toilet article illustrated in FIGS. 9, 10 or 11 is used, the releasing sheet 4 is first removed from the article, and then water, toilet water, lotion or milky lotion is applied to the surface of the hydrogel formable polymer layer 3 or the surface of the cosmetics 9.

As a result of the application and absorption of water, the hydrogel formable polymer layer 3 forms gel and swells. Under this condition, the toilet article is applied to the objective portion of a person, and the pressure sensitive adhesive layer at the peripheral portion of the toilet article is urged to the skin by pressing the article on the back of the sheet so as to fix the article there.

In the embodiments illustrated in FIGS. 9, 10 and 11, the hydrogel formable polymer layer 3 is attached to the pressure sensitive adhesive layer 2 while a part of the pressure sensitive adhesive layer 2 is left free similar to that illustrated in FIG. 1. It is possible to form the hydrogel formable polymer layer 3 on the entire surface of the pressure sensitive adhesive layer 2 and provide the article with a suitable means for fixing the article to the skin, such as a strand-like material or a tape-like material having adhesive coating thereon, similar to the embodiments illustrated in FIGS. 7 and 8.

Further, the embodiments illustrated in FIGS. 9, 10 and 11 are usable and portable, since the cosmetics have previously been contained in or adhered to the hydrogel formable polymer layer. In other words, the toilet article illustrated in FIGS. 9, 10 and 11 are convenient to use during journeys, since only application of water to the hydrogel formable polymer layer is sufficient to use them, and accordingly, it is unnecessary to bring toilet water or milky lotion bottled in a vessel which has conventionally been indispensable.

As described above, the toilet article of the present invention can be an effective tool for beauty treatment wherein the characteristics of the hydrogel formable polymer is fully utilized to last for a long time the effects of the cosmetics for refreshing the skin and the effects of packing the facial skin. More specifically, if the toilet article of the present invention is used before going to bed, the cosmetics do not dry for a long time during a sleep and contacts the skin to achieve its effects.

From the practical use, it has confirmed that the article of the present invention can be used not only as a tool for refreshing the skin but also as a tool for packing the facial skin or healing the skin disease caused by sunburn in the summer.

In addition, the article of the present invention can be used as a medical tool for remedying bruise or sprain, i.e, for applying poultice, if endothermic compound is contained therein. Thus, according to the present invention, a valuable article is presented.

I claim:

1. A cosmetic article comprising a sheet-like material, an adhesive layer formed on said sheet-like material, and a sheet consisting essentially of at least one hydrogel formable polymer selected from the group consisting of crosslinked alkali metal salts of carboxymethylcellulose and crosslinked polyalkylene oxide on said adhesive layer, said sheet of hydrogel formable polymer being present in an essentially dry condition but having the property of swelling and forming a gel when water at ambient temperature or a substance containing water is applied, said gel retaining at least 10 times its weight of water.

2. A cosmetic article according to claim 1 further comprising a releasing sheet covering said hydrogel formable polymer sheet and said adhesive layer.

3. A cosmetic article according to claim 1 further comprising a porous layer formed between said adhesive layer and said hydrogel formable polymer sheet.

4. A cosmetic article according to claim 1 further comprising a porous layer formed on said hydrogel formable polymer sheet.

5. A cosmetic article according to claim 1 further comprising a porous layer, formed between said adhesive layer and said hydrogel formable polymer sheet, and another porous layer, formed on said hydrogel formable polymer sheet.

6. A cosmetic article according to claim 5 wherein a bonded area is formed at outer edges of said porous layers overlapping with each other.

7. A cosmetic article according to claim 1, which includes a plurality of hydrogel formable polymer sheets.

8. A cosmetic article according to claim 1 further comprising a means for fixing said article to a predetermined portion of a person.

9. A cosmetic article according to claim 8 wherein said adhesive layer formed on said sheet-like material comprises pressure sensitive adhesive, a part of said pressure sensitive adhesive layer is capable of being exposed to outside in use and forms said fixing means.

10. A cosmetic article according to claim 8 wherein said fixing means is at least one elongated material, one end of which is fixed to said article.

11. A cosmetic article according to claim 10 wherein said elongated material has a pressure sensitive adhesive coated thereon.

* * * * *